United States Patent [19]

Chu et al.

[11] Patent Number: 5,426,214

[45] Date of Patent: Jun. 20, 1995

[54] PROPYLENE GLYCOL MONOMETHYL ETHER BUTYRATES AND ISOMERS, AND THE PROCESS FOR THE PREPARATION THEREOF

[75] Inventors: Tzong-Jeng Chu, Tainan; Neng-Hui Chu, Kaohsiung Hsien; Huang Kuo-Chu, Kaohsiung; Chin Y. Lee, Taipei, all of Taiwan, Prov. of China

[73] Assignee: Shiny Chemical Industrial Co., Ltd., Kaohsiung Hsien, Taiwan, Prov. of China

[21] Appl. No.: 236,712

[22] Filed: Apr. 29, 1994

[51] Int. Cl.$^6$ .................... C07C 67/28; C07C 67/00
[52] U.S. Cl. ................................................ 560/263
[58] Field of Search ......................................... 560/263

[56] References Cited

U.S. PATENT DOCUMENTS

| | | | |
|---|---|---|---|
| 5,087,659 | 2/1992 | Fujisawa | 524/594 |
| 5,247,029 | 9/1993 | Nishida et al. | 525/526 |
| 5,283,124 | 2/1994 | Fujibayashi et al. | 523/404 |

*Primary Examiner*—Arthur C. Prescott
*Attorney, Agent, or Firm*—Pro-Techtor International

[57] ABSTRACT

Propylene glycol monomethyl ether butyrates and their isomers are obtained by the esterification of propylene glycol monomethyl ether or its isomer with iso-butyric or n-butyric acid at an elevated temperature above 80° C. in the presence of acidic catalyst and azeotropic agent. These compounds are rectified for removing acid residue and moisture in order to yield the desirable product having high purity.

11 Claims, 4 Drawing Sheets

PROPYLENE GLYCOL MONOMETHYL ETHER BUTYRATES AND ISOMERS, AND THE PROCESS FOR THE PREPARATION THEREOF

FIELD OF THE INVENTION

This invention relates to propylene glycol monomethyl ether butyrates obtained by the reaction between propylene glycol monomethyl ether and iso-butyric or n-butyric acid as starting materials.

The so-called propylene glycol monomethyl ether butyrates comprises iso-butyrate having the formula (I):

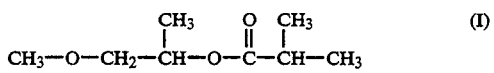

and its isomer having the formula (II):

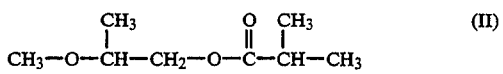

as well as n-butyrate having the formula (III):

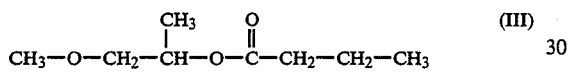

and its isomer having the formula (IV):

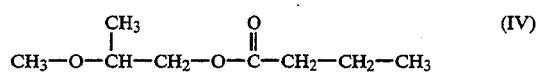

BACKGROUND OF THE INVENTION

Organic ester compounds are good solvents used in quantities in synthetic resin industries, such as for paints, inks, adhesives and detergents. At present, ether compounds are mainly divided into two categories, i.e. E series and P series. The E series of ether compounds are obtained from the synthesis of alcohols and ethylene oxide while P series of ether compounds are obtained from the synthesis of alcohols and propylene oxide. For example, the P series of ether compounds obtained from the synthesis of methanol and propylene oxide will produce two isomers, one of which is 1-methoxy-2-propanol having the structural formula:

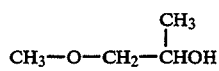

and other is 2-methoxy-1-propanol having the structural formula:

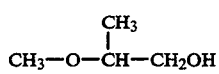

with a proportion of the former to the later in 98:2. The former is dominant and thus commonly referred as propylene glycol monomethyl ether.

SUMMARY OF THE INVENTION

An object of the present application is to provide the novel propylene glycol monomethyl ether butyrate compounds.

Another object is to provide a process for the preparation of propylene glycol monomethyl ether butyrates, either iso-butyrate (called PMIB hereunder) and its isomer or n-butyrate (called PMB hereunder) and its isomer, which comprises reacting propylene glycol monomethyl ether (called PGM hereunder) obtained by the reaction of methanol and propylene oxide under high pressure at high temperature with iso-butyric or n-butyric acid in the presence of acidic catalyst.

Further object is to use PMIB and PMB as solvents, especially in the fields of paints, inks, adhesives and detergents inductries.

DETAILED DESCRIPTION OF PREFERRED EMBODIMENTS

Figure 1:
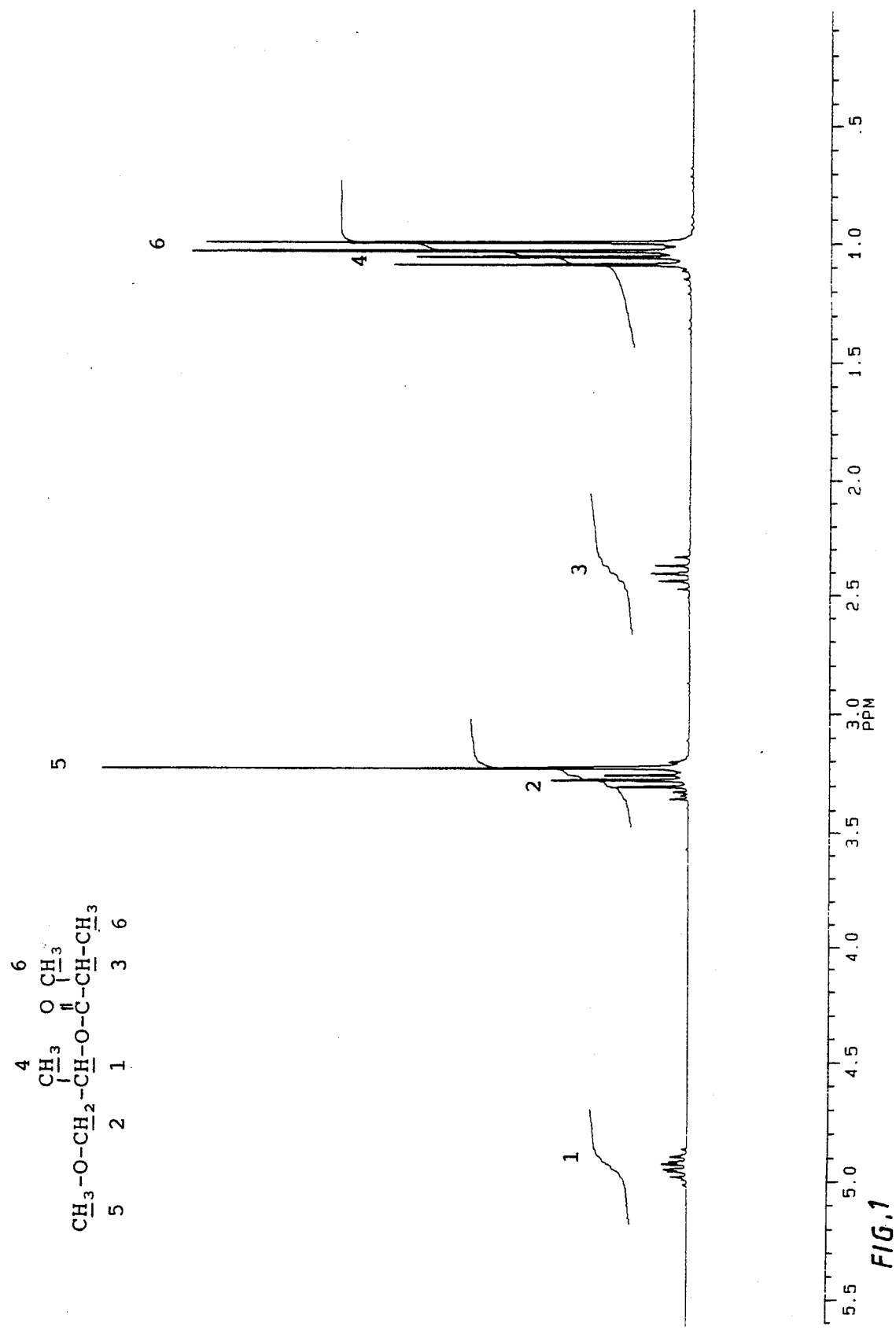
FIG. 1 shows a NMR'H spectrum of PMIB produced according to the present invention.

The process for the preparation of PMIB or PMB according to the present invention consists of batch and continuous processes. In general when the moisture generated during the reaction is not removed, the reaction system is likely reached an equilibrium state which would hinder the increase of productivity and thus disadvantageous to industrial production. Therefore, in the process of the present invention, no matter whether batch or continuous process is adopted, the reaction system may be added with aromatic compound, such as, for example, benzene, toluene, xylene and cyclohexane, as an azeotropic agent. The azeotropic component so added must be incompatible with water and has azeotropic effect with water. Aromatic compound is good in meeting these requirements.

In the batch process, the reactants and azeotropic solvent are placed into the reactor for carrying out the reaction at the azeotropic temperature while removing the water and recycling the azeotropic solvent. After the end of the reaction, the products and azeotropic solvent are separated by fractionating distillation so as to obtain the products of high purity.

In the continuous process, the starting materials are fed at a given flow rate on the one hand, and the water is withdrawn continuousely from the top of the fractionator during process of the reaction on the other hand. The azeotropic solvent is recycled while the reaction system containing the products PMIB or PMB in a concentration of a certain extent presented in the reactor is transferred in to a rectifying tower in order to proceed the fractionating distillation to remove a minor amount of unreacted ether, acid and PMIB or PMB. Thereby, a product of high purity is obtained.

According to the process for the preparation of PMIB or PMB in the present application, the starting materials of PGM and iso-butyric or n-butyric acid are reacted at an elevated temperature above 80° C. in the presence of acidic catalyst and azeotropic agent for taking place the esterification to produce crude PMIB or PMB. The products are then separated by rectification for removing the unreacted acid and generated water to obtain PMIB or PMB of high purity.

For the starting materials, the molar ratio of PGM to iso-butyric or n-butyric acid is generally in the range of 0.6 to 3.0, preferably from 1.1 to 1.5, in which PGM is in excess with respect to iso-butyric or n-butyric acid. If the molar ratio is smaller than 0.6 or greater than 3.0, after the reaction is accomplished, either party in the reaction system will leave unreacted residue in great excess so that not only more energy consumption will be rendered during the rectifying process, but also the rectifying time required is increased so as to decrease the production. If iso-butyric or n-butyric acid is excess too much, namely the molar ratio smaller than 0.6, the reaction rate will be remarkably dropped. The reason is unclear but it is assumed that the acidic catalyst is subjected to buffering.

The catalysts used in the present invention include inorganic acids, such as sulfuric acid, hydrochloric acid and phosphoric acid, and organic acids, such as acetic acid, oxalic acid, citric acid, p-toluene sulfonic acid and methane sulfonic acid, among which the strong acids including sulfuric acid, p-toluene sulfonic acid and methane sulfonic acid are preferred. The boiling points of propylene glycol monomethyl ether iso-butyrate and n-butyrate obtained according to the present application are 167.2° C. and 180.5° C., respectively, while other reactants and products having respective boiling point of 120° C. for PGM, 154.4° C. for iso-butyric acid, 164° C. for n-butyric acid and 100° C. for water. It is apparently easier to rectify this solution comparing the respective boiling point of 146° C. for propylene glycol monomethyl ether acetate, 118° C. for acetic acid and 120° C. for PGM as in the conventional case. This is one of the effect achieved by the process according to the present invention.

Another effect achieved is lower toxicity of PMIB and PMB against the metabolic organs. In accordance with NOEL (No Observable Effect Level) published by Environment Protection Agency of U.S.A., E and P series of esters for rabbit are 30 and 3000 ppm, respectively. PMIB and PMB of this invention belong to P series and thus has very low toxicity against to genital organ.

Further, PMIB and PMB have better solubility to various resins. For example, propylene glycol monomethyl ether acetate has final solvent percentage of 70% to alkyd resin while present propylene glycol monomethyl ether butyrates and their isomers are over 90%, an excellent solvent is herewith proved.

In the process of the present invention, when the reaction is completed the reaction system must be treated by double rectification. Primary rectification is a dehydration and deacidification procedures. For enhancing the efficiency and saving the energy, an azeotropic agent selected from aromatic organic solvent comprising benzene, toluene, xylene and cyclohexane is added in amount of 8 to 20% with respect to the combined starting materials in order to reduce the azeotropic temperature in rectification. At secondary rectification, only two components of ether and ester are left, which are likely completely fractionally distilled based on the difference of boiling points between two components, thereby a product of high purity is obtained.

Now, the present invention will be further described by means of the following Examples which are merely for the purpose of illustration and by no means of any limitation therefor.

EXAMPLE 1

Into the reactor having a volume of 3 liters, 1056.5 g of PGM and 688.5 g of iso-butyric acid were introduced. After mixing 200 ml of xylene and 10 grams of p-toluene sulfonic acid were added. Then the temperature was brought of reflux temperature at 92° C. to carry out the reaction for 5 hours. During this period the dehydration was taken place simultaneously in favor of the progression of the reaction. The reaction solution was analyzed by gas chromatography and found the following composition:

| PMIB | 67.45% |
|---|---|
| PGM | 18.66% |
| iso-butyric acid | 4.33% |
| xylene | 8.97% |
| water | 0.59% |

This solution was further treated by double rectification, PMIB compound having a purity greater than 99.9% was obtained.

Figure 2:
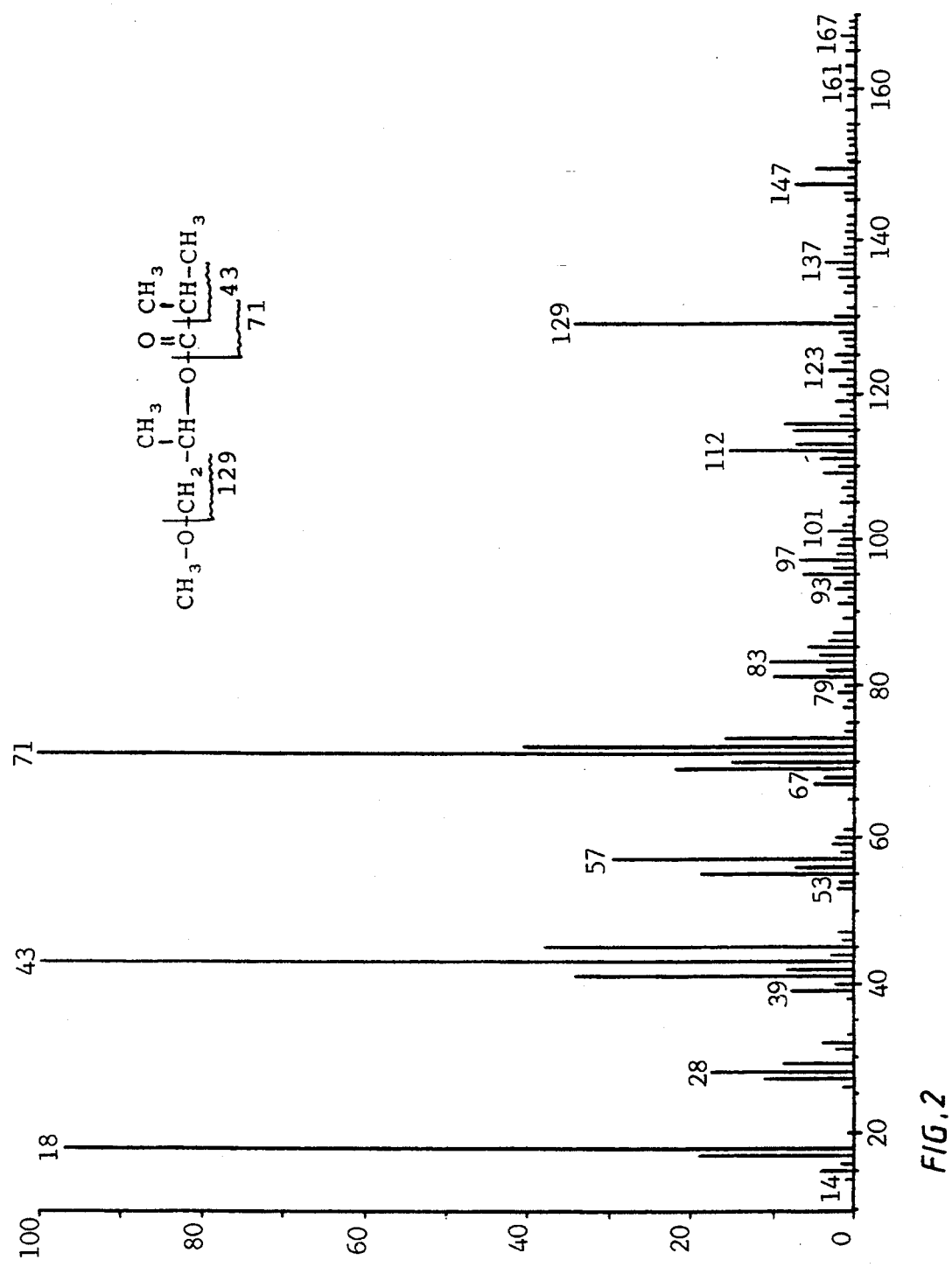
FIG. 2 shows a mass spectrum of PMIB produced according to the present invention.

This PMIB compound was characterized by NMR'H spectrum as shown in FIG. 1 and mass spectrogram as shown in FIG. 2, thereby the chemical structure thereof can be determined as

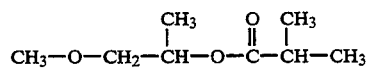

while trace of isomer having the structure:

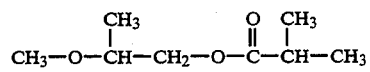

is not readily to be detected in the spectra.

EXAMPLE 2

Into the reactor having a volume of 3 liters, 1056.5 g of PGM and 688.5 g of n-butyric acid were introduced. After mixing 200 ml of xylene an 10 grams of p-toluene sulfonic acid were added. Then the temperature was brought to reflux temperature at 105° C. to carry out the reaction for 5 hours. During this period the dehydration was taken place simultaneously in favor of the progression of the reaction. The reaction solution was analyzed by gas chromatography and found the following composition:

| PMB | 68.20% |
|---|---|
| PGM | 18.46% |
| n-butyric acid | 4.20% |
| xylene | 8.55% |
| water | 0.59% |

This solution was further treated by double rectification, PMB compound having a purity greater than 99.9% was obtained.

Figure 3:
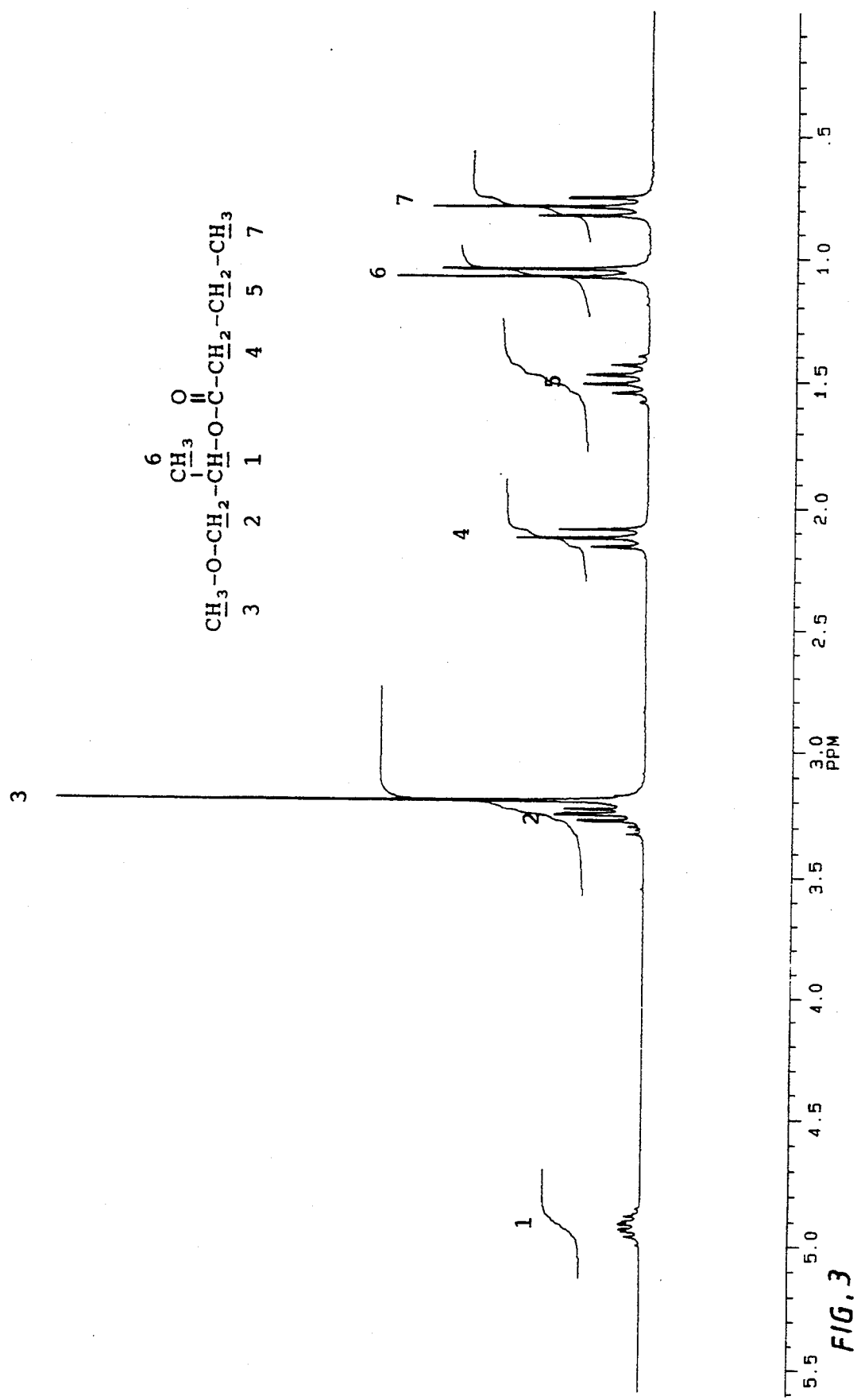
FIG. 3 shows a NMR'H spectrum of PMB produced according to the present invention.
Figure 4:
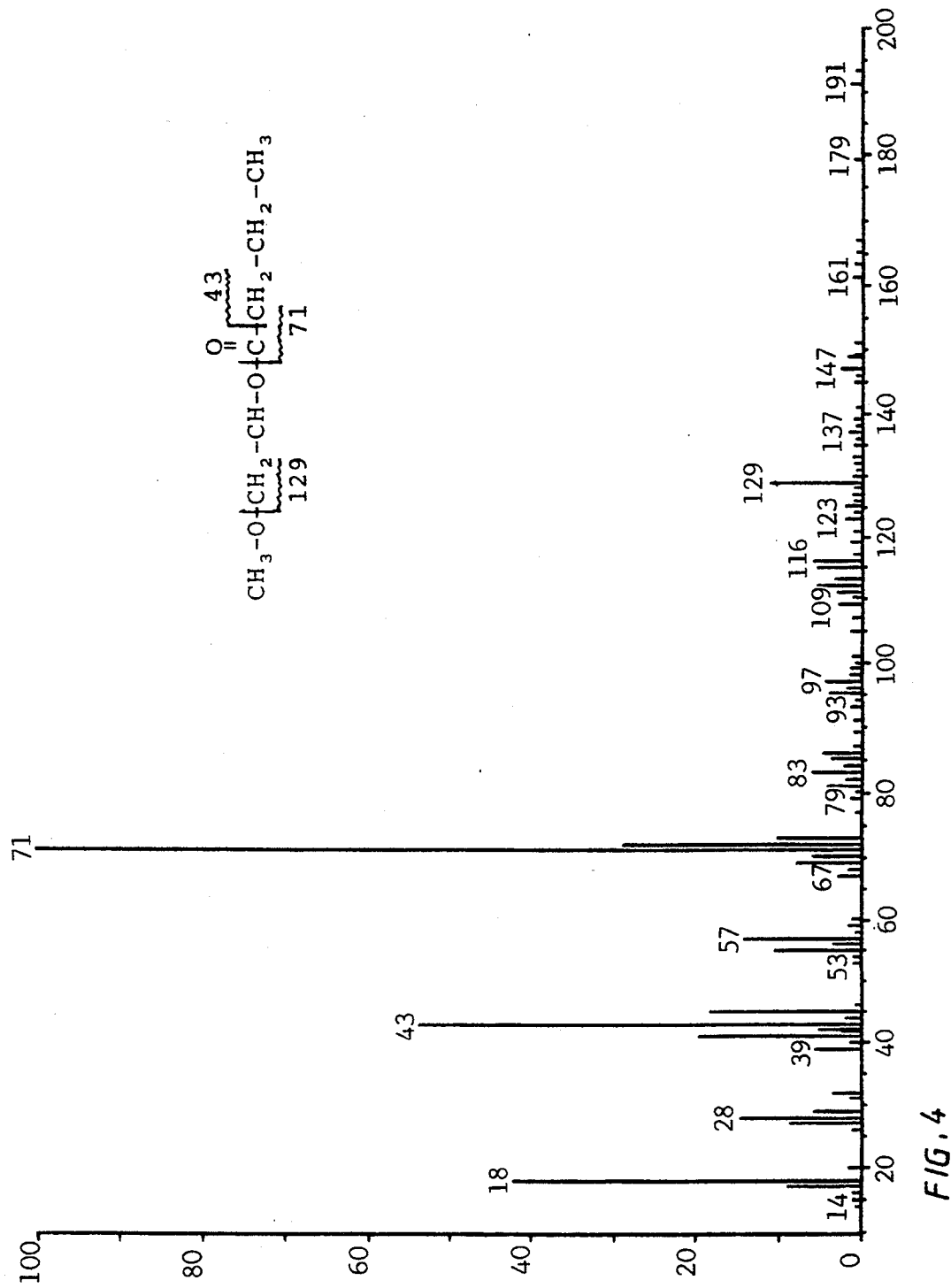
FIG. 4 shows a mass spectrum of PMB produced according to the present invention.

This PMB compound was characterized by NMR'H spectrum as shown in FIG. 3 and mass spectrogram as shown in FIG. 4, thereby the chemical structure thereof can be determined as

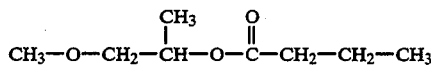

while trace of isomer having the structure:

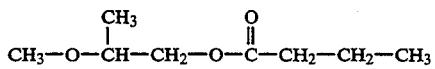

is not readily to be detected in the spectra.

EXAMPLE 3

Into the reactor having a volume of 3 liters, 1056.5 g of PGM and 688.5 g of iso-butyric acid were introduced. After mixing 10 grams of p-toluene sulfonic acid were added. Then the temperature was brought to 99.3° C., the azetropic temperature of water and iso-butyric acid, to carry out the reflux reaction for 5 hours. Since no azeotropic solvent was added, the aqueous layer was impossibly separated, therefore the equilibrium was likely reached. This reaction solution was analyzed by gas chromatography and found the following composition:

| | |
|---|---|
| PMIB | 41.1% |
| PGM | 38.4% |
| iso-butyric acid | 13.9% |
| water | 6.6% |

EXAMPLE 4

Into the reactor having a volume of 3 liters, 1056.5 g of PGM and 688.5 g of n-butyric acid were introduced. After mixing 10 grams of p-toluene sulfonic acid were added. Then the temperature was brought to 99.3° C., the azeotropic temperature of water and n-butyric acid, to carry out the reflux reaction for 5 hours. Since no azeotropic solvent was added, the aqueous layer was impossibly separated, therefore the equilibrium was likely reached. This reaction solution was analyzed by gas chromatograhy and found the following composition:

| | |
|---|---|
| PMB | 41.8% |
| PGM | 38.0% |
| n-butyric acid | 13.4% |
| water | 6.8% |

COMPARATIVE EXAMPLE

Into the reactor having a volume of 3 liters, 1172 ml of PGM and 572 ml of acetic acid were introduced. After mixing 10 grams of p-toluene sulfonic acid were added. Then the temperature was brought to the reflux temperature of 97.5° C. to carry out the reaction for 5 hours. The reaction solution was analyzed by gas chromatography and found the following composition:

| | |
|---|---|
| propylene glycol monomethyl ether acetate | 44.0% |
| acetic acid | 20.1% |
| PGM | 29.7% |
| water | 5.8% |

This solution was treated by double rectification, propylene glycol monomethyl ether acetate having a purity of 99% was obtained. The yield is too low to meet the industrial requirement.

We claim:

1. Propylene glycol monomethyl ether iso-butyrate and the isomer thereof.

2. Propylene glycol monomethyl ether n-butyrate and the isomer thereof.

3. The propylene glycol monomethyl iso-butyrate and the isomer thereof according to claim 1, produced by the reaction between propylene glycol monomethyl ether and iso-butyric acid.

4. The propylene glycol monomethyl n-butyrate and the thereof according to claim 2 produced by the reaction between propylene glycol monomethyl ether and n-butyric acid.

5. A process for the preparation of propylene glycol monomethyl ether iso-butyrate and its isomer or n-butyrate and its isomer, comprising the steps of reacting propylene glycol monomethyl ether and iso-butyric or n-butyric acid at elevated temperature above 80° C. in the presence of acidic catalyst and azeotropic agent to promote esterification, to produce crude propylene glycol monomethyl ether iso-butyrate or propylene glycol monomethyl ether n-butyrate and removing the unreacted acid and water by distillation to obtain propylene glycol monomethyl ether iso-butyrate and its isomer or propylene glycol monomethyl ether n-butyrate and its isomer having high purity.

6. The process according to claim 5, wherein the molar ratio between propylene glycol monomethyl ether and iso-butyric or n-butyric acid is in the range of from 0.6 to 3.0.

7. The process according to claim 5, wherein said catalyst is a strong acid selected from a group consisting of sulfuric acid, p-toluene sulfonic acid and methane sulfonic acid.

8. The process according to claim 5, wherein said azeotropic agent is selected from a group consisting of benzene, toluene, xylene and cyclohexane.

9. The process according to claim 8, wherein said azeotropic agent is used in an amount of 6% to 30% by volume with respect to the sum of propylene glycol monomethyl ether and iso-butyric or n-butyric acid.

10. The use of propylene glycol monomethyl ether iso-butyrate or n-butyrate as a solvent.

11. The use according to claim 10 as a solvent for paints, inks, adhesives or detergents and the like.

* * * * *